US008039427B2

(12) United States Patent
Egan et al.

(10) Patent No.: US 8,039,427 B2
(45) Date of Patent: Oct. 18, 2011

(54) METHOD FOR MANUFACTURING A SHAPED ARTICLE

(75) Inventors: Stefan James Egan, Newcastle Upon Tyne (GB); Michael McDonnell, Blyth (GB); Sanjeev Sharma, Newcastle Upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 523 days.

(21) Appl. No.: 11/999,622

(22) Filed: Dec. 6, 2007

(65) Prior Publication Data

US 2009/0023621 A1 Jan. 22, 2009

(30) Foreign Application Priority Data

Dec. 6, 2006 (EP) .................................... 06125515

(51) Int. Cl.
*A61K 7/50* (2006.01)

(52) U.S. Cl. ......... 510/445; 510/446; 510/447; 510/451

(58) Field of Classification Search .................. 510/445
See application file for complete search history.

(56) References Cited

U.S. PATENT DOCUMENTS

| | | | |
|---|---|---|---|
| 2,343,829 | A | 3/1944 | Benjamin |
| 6,747,000 | B2 | 6/2004 | Pearce et al. |

FOREIGN PATENT DOCUMENTS

| | | | |
|---|---|---|---|
| WO | WO 97/33965 | A1 | 9/1997 |

OTHER PUBLICATIONS

PCT International Search Report dated Jun. 12, 2006-3 pgs.

*Primary Examiner* — Necholus Ogden, Jr.
(74) *Attorney, Agent, or Firm* — Julie A. McConihay; Leonard W. Lewis; Steven W. Miller

(57) ABSTRACT

A method for manufacturing a shaped article comprising the step of cutting a shaped article from a first article; wherein as the shaped article is cut from the first article the shaped article's cross-section is deformed and wherein the first article's cross-section is shaped such that it compensates for the deformation during the cutting step so as to achieve a shaped article with a desired cross-section. Shaped articles and compositions comprising shaped articles are also described.

4 Claims, No Drawings

METHOD FOR MANUFACTURING A SHAPED ARTICLE

FIELD OF THE INVENTION

The present invention is in the field of shaped article manufacture, in particular it relates to a method for manufacturing a shaped article. The invention also relates to shaped articles and compositions containing them, particularly detergent compositions.

BACKGROUND OF THE INVENTION

For many years coloured particles have been incorporated into cleaning compositions for improving the aesthetics of the cleaning composition. Traditionally, these aesthetic particles are coloured detergent particles for example as described in WO 97/33965. They may also be in the form of noodles as described in U.S. Pat. No. 6,747,000.

The present invention seeks to provide improved aesthetic particles for use in consumer products, particularly cleaning compositions. However, producing shaped articles with complicated cross-sections is technically challenging. The process must be efficient and able to produce aesthetic particles at high speed, but also the aesthetic particles must have a good, reliable shape and meet the technical requirements of the end uses. For example, they may be required to dissolve during a washing process, such as a laundry washing process, whilst being robust enough to withstand handling and storage without breaking. These technical challenges are exacerbated because such particles are typically small, for example having a greatest cross-section of below 8 mm, usually below 6 mm or 5 mm or 4 mm.

SUMMARY OF THE INVENTION

In accordance with the present invention there is provided a method for manufacturing a shaped article comprising the step of cutting a shaped article from a first article; wherein as the shaped article is cut from the first article the shaped article's cross-section is deformed; and wherein the first article's cross-section is shaped such that it compensates for the deformation during the cutting step so as to achieve a shaped article with a desired cross-section. The present invention also provides a shaped article obtainable by said method of manufacture and detergent compositions comprising them. This method has been found to provide an efficient, reliable means of preparing shaped articles having a variety of shapes which may be relatively complex and through which a desired shape is achieved.

In another aspect of the present invention a composition for manufacturing a shaped article is provided. The composition typically comprises soap. Preferred compositions for use herein comprise from 60% to 99% by weight of soaps of $C_8$-$C_{20}$ fatty acids. Typically the compositions may comprise from 0.1% to 20% by weight of water. Preferred compositions also comprise an inorganic salt, for example from 0.05% to 5% by weight of an inorganic salt, preferably sodium chloride. Preferred compositions also comprise glycerine, typically from 0.01% to 10% by weight of glycerine. Such soap-containing compositions will typically comprise less than 5% by weight of free fatty acids. Such compositions have been found to provide highly satisfactory shaped particles, for example providing an excellent balance between low deformability during cutting, good dissolution and frangibility. The presence of glycerine in the composition may be particularly advantageous as it may also improve the colouring of the composition if a colorant is incorporated.

In another aspect of the present invention, a method for manufacturing a shaped article comprising the step of cutting a shaped article from a first article using a tapered blade holder is provided. Preferably, the blade is tension mounted. The use of a tapered blade holder has surprisingly been found to alleviate the problem of post-cutting deformation of the shaped article.

In a preferred embodiment of the present invention, the first article's cross-section is greater, with respect to the desired cross-section of the shaped article, in the cutting direction. In a further preferred embodiment of the present invention the method comprises the step of forming the first article by extrusion. Preferably, the shaped article is cut from the first article as it is extruded.

DETAILED DESCRIPTION OF THE INVENTION

Definitions

When used herein the term "cutting direction" refers to the direction in which the blade moves through the first article while forming the shaped article. The "cutting plane" refers to the plane parallel to the cutting direction. The "length of the shaped article" refers to the length of the shaped article in the direction normal to the cutting plane and, when extruded, preferably the length of material extruded before the cutting step. When used herein the term "cross-section" refers to the shape of the face of either the shaped or first articles (as referred to) which is parallel to the cutting plane.

Shaped and First Articles

First article describes any body of material from which a further article may be cut. Shaped article describes any article cut from a first article.

The method according to the invention for forming the shaped articles of the present invention may be a batch or a continuous process, continuous processes are preferred as a higher production rate can be achieved.

The first article of the present invention may typically be formed by extrusion. Typically, extrusion is understood to mean any process by which a body of material is forced through a die or orifice so as to form a length of extruded material. In the case of the present invention the extrusion will normally be performed using a commercially available extruder, such as a screw extruder. Commercially available screw extruders typically comprise one or more feeders or hoppers, for storing the material prior to extrusion; a barrel which houses one or more screws; and a die through which the material is extruded. The screws are rotated and the material is typically heated and/or kneaded and/or compacted as it is drawn through the barrel. Typically, the material is forced through the one or more dies, which are usually situated at the end of the barrel furthest from the one or more feeders. It is preferable to use more than one die as this increases the number of first articles, and thus shaped articles, which can be produced at any one time. In a preferred embodiment of the present invention the extruder die comprises greater than or equal to 50 orifices, preferably greater than or equal to 100 orifices and even more preferably greater than or equal to 200 orifices. The shape of the one or more dies' orifices' will determine the cross-section and/or shape of articles extruded therefrom. The screw configuration is typically chosen depending on how deformable the material is and at what temperature the material is mobile enough to be properly compacted and extruded. In certain embodiments of the present invention the temperature of the extrudate may typically be from 70° C. to 130° C., or from 80° C. to 120° C. or even from 90° C. to 110° C. Screw configurations can be chosen with varying amounts of back-flow, sheer, compaction, heat and combinations thereof. Commercially available screw extruders suitable for use in the present invention include but are not limited to the TX-85 Twin Screw Extruder manufactured by Wenger.

When extrusion is used to form the first article, it is preferable for the shaped article to be cut from the first article as it is extruded. This is understood to mean that as the material leaves the die it is cut immediately to form the shaped articles, as opposed to lengths of material being formed which are then stored and cut at a later time. Typically, the first article (the extrudate) will be cut when the length of extrudate equal to the desired length of the shaped article has been extruded.

Typically the shaped article will be cut from the first article by running the blade flush to the die. Preferably the blade will be tension mounted against the die's surface so as to ensure it runs as closely over the face of the die as possible. It is of course understood that in other embodiments of the invention, the material may be formed into extended lengths of material and cut at a later time.

The shaped articles may have any preferred cross-section. Particularly preferred shaped article cross-sections are annular, other preferred cross-sections include any letter of the alphabet, stars, triangles, squares, pentagons, hexagons, heptagons, octagons, non-geometric shapes including for example shapes of animals, birds or other living things, cartoons, flowers, moons, discs, crosses and any other desired shape. In certain embodiments the shaped articles may of course be non-annular. In a preferred embodiment of the present invention the shaped article will have an extruded length (i.e. the length of the shaped article) of from 0.05 mm to 1 mm, preferably from 0.1 mm to 0.75 mm and most preferably from 0.2 mm to 0.5 mm. In certain embodiments, the length of the shaped article will generally be equal to the length of material extruded prior to the cutting step taking place.

In the preferred embodiments of the present invention where the first article is formed by extrusion it is preferable for the orifice of the die to be shaped such that is compensates for the deformation during the cutting step so as to achieve a shaped article with a desired cross-section.

As discussed above, in a preferred embodiment of the present invention the first article's cross-section is greater, with respect to the desired cross-section of the shaped article, in the cutting direction. In the embodiments of the present invention where the first article is formed by extrusion it is preferable that the orifice through which the composition is extruded is orientated such that the orifice's greatest cross-section is substantially parallel to the cutting direction.

In a further embodiment of the present invention the ratio between the length of the shaped article to its greatest cross-section is from about 1:1 to about 1:100, or even from about 1:5 to about 1:50, or even from about 1:10 to about 1:20.

The shape of the die's orifice will depend upon the shape of the desired shaped article, and the compensation for deformation or cutting. In one embodiment of the present invention the ratio of the diameter of the first article's cross-section in the cutting direction to the diameter of shaped article's cross-section in the cutting direction is greater than 1. Preferably the ratio will be from 5:1 to 101:100 or even from 3:1 to 11:10 or even from 1.5:1 to 1.05:1.

In a particularly preferred embodiment the desired shaped article comprises a circular ring and an elliptical ring orifice is used to form an elliptical tube-shaped first article from which substantially circular ring-shaped articles are cut. In a particularly preferred embodiment of the present invention a die having at least one elliptical orifice is used. Preferably said elliptical orifice will have a greatest diameter of from 2 mm to 8 mm, preferably from 3 mm to 7 mm, and a smallest diameter of from 1 mm and 5 mm, preferably from 2 mm and 4 mm. In a particularly preferred embodiment the elliptical orifice will have an elliptical central pin inserted within the orifice so as to form an elliptical annular orifice. Preferably, said elliptical central pin will have a greatest diameter of from 0.5 mm to 7.5 mm, preferably from 2.5 mm to 5 mm, and a smallest diameter of from 0.25 mm to 3.5 mm, preferably from 0.5 to 2 mm. The particular shape of the die orifice required to achieve the desired shaped article will depend on a number of factors including the extrudate composition, the extrudate viscosity, the cutting speed and the length of the shaped articles.

When used herein the term blade will be understood to have its normal meaning in the art and will include any means which may be used to cut, cleave or generally remove a shaped article from a first article; typically, including a knife. Particularly preferred blades for use herein are those mounted on rotary cutters. Rotary cutters comprise a number of individual blades fixed to a device having an axle. The device is rotated about the axle, with the blades aligned such that they are at a generally normal angle to the direction of rotation. Thus, a number of blades can be made to pass over a single location in a short period of time; allowing a great number of shaped articles to be cut from first articles in quick succession. Typically, when rotary cutters are used in the present invention they may comprise more than one blade, preferably more than or equal to five blades, more preferably more than or equal to ten blades and most preferably more than or equal to fifteen blades. Typically the rotary cutters will be rotated at greater than or equal to 1000 revolutions per minute (rpm), preferably greater than or equal to 2000 rpm and even more preferably greater than or equal to 3000 rpm. In a particularly preferred embodiment of the present invention the rotary cutter may be located directly adjacent to the die of the extruder, where it will cut the shaped articles from the first articles as they are extruded. Preferably the rotary cutter is located such that the blades are flush to the extruder die and even more preferably they are tension mounted against the die. Particularly preferred rotary cutters and blades are commercially available such as those from Wenger or de Souza.

In a preferred embodiment of the present invention the angle of the blade with respect to the cutting plane will be less than or equal to 45°, or even less than or equal to 25°, or even more less than or equal to 15°. By using lower blade angles it has been found that the shaped article it deformed less during the cutting step.

In a preferred embodiment of the present invention the one or more blades may be held by blade holders. Particularly preferred blade holders are tapered blade holders. A tapered blade holder is understood to mean any blade holder which is designed such that it will not deform the shaped article once the shaped article has been cut from the first article. Preferred tapered blade holders for use herein will cover a portion of the blade and will not form an abrupt edge with the uncovered portion of the blade. Particularly, preferred tapered blade holders will have an upper surface which intercepts the upper surface of the blade at an angle of less than 90°, preferably less than 45°, even more preferably less than 30° and most preferably less than 20°. The tapered blade holder may have a concave curved upper surface, such that the angle of the blade holder surface to the blade increases exponentially as the distance from the blade tip increases.

Compositions

Typically, the shaped article and the first article will comprise substantially the same composition. Preferably, the composition will comprise at least one component suitable for use in a detergent composition, preferably a laundry detergent composition. It is particularly preferred that at least one of the components suitable for use in a detergent composition is a soap. Soap is understood to have its ordinary meaning in the art. Particularly preferred soaps for use in the present invention are soaps of $C_8$-$C_{20}$ fatty acids.

Preferred compositions for use herein comprise from 60% to 99% or even 70% to 95% or even from 80% to 90% by weight of soaps of $C_8$-$C_{20}$ fatty acids. Typically the compositions may comprises from 0.1% to 20%, or even from 1% to 15% or even from 5% to 10% by weight of water. Preferred compositions also comprise an inorganic salt, for example from 0.05% to 5%, or even from 0.1% to 3%, or even from 0.5% to 2% and or even from 0.65% to 1% by weight of an inorganic salt, preferably sodium chloride. Preferred compositions also comprise glycerine, typically from 0.01% to 10%, or even from 1% to 5% and or even from 2% to 4% by weight of glycerine. Such soap-containing compositions will typically comprise less than 5% or even less than 1% and or even 0% by weight of free fatty acids. Such compositions have been found to provide highly satisfactory shaped particles, for example providing an excellent balance between low deformability during cutting, good dissolution and frangibility. The presence of glycerine in the composition may be particularly advantageous as it may also improve the colouring of the composition if a colorant is incorporated.

Particularly preferred compositions of soaps of $C_8$-$C_{20}$ fatty acids comprise from 1% to 2% by weight of $C_8$ fatty acids, from 1% to 2% by weight of $C_{10}$ fatty acids, from 8% to 12% by weight of $C_{12}$ fatty acids, from 4% to 6% by weight of $C_{14}$ fatty acids, from 0% by weight of $C_{15}$ fatty acids, from 0.2% to 2% by weight of $C_{16'}$ fatty acids (' refers to the number of carbon double bonds present in the carbon chains), from 25% to 35% by weight of $C_{16}$ fatty acids, from 4% to 8% by weight of $C_{18''}$ fatty acids, from 30% to 35% by weight of $C_{18'}$ fatty acids and from 6% to 10% by weight of $C_{18}$ fatty acids. Preferred sources of fatty acid soaps are beef tallow, coconut oil and palm oil soaps.

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The adjuncts may be incorporated either as part of the compositions from which the shaped articles are made or as part of a detergent composition comprising the shaped articles formed by the process of the present invention. The shaped articles obtainable by the method of the present invention may be for use in any consumer product, though typically it will be for incorporation into any cleaning compositions, especially laundry detergents and for dishwashing detergents in any physical form such as liquids, gels, particles, tablets etc. The precise nature of these additional adjunct components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference. When one or more adjuncts are present, such one or more adjuncts may be present as detailed below:

Adjuncts

Bleaching Agents—The cleaning compositions of the present invention may comprise one or more bleaching agents. Suitable bleaching agents other than bleaching catalysts include other photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) other photobleaches for example Vitamin K3;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject composition.

Builders—The cleaning compositions of the present invention may comprise one or more detergent builders or builder systems. When a builder is used, the subject composition will typically comprise at least about 1%, from about 5% to about 60% or even from about 10% to about 40% builder by weight of the subject composition.

Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The cleaning compositions of the present invention will preferably also contain additional components that may tint articles being cleaned, such as fluorescent whitening agent. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of:

4,4'-bis-(2-diethanolamino-4-anilino-s-triazin-6-ylamino) stilbene-2,2'-disulphonate, 4,4'-bis-(2,4-dianilino-s-triazin-6-ylamino) stilbene-2,2'-disulphonate, 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate, 4,4'-bis-(2-anilino-4(1-methyl-2-hydroxy-ethylamino)-s-triazin-6-ylamino) stilbene-2,2'-disulphonate and, 2-(stilbyl-4"-naptho-1,2':4,5)-1,2,3-trizole-2"-sulphonate.

Preferred fluorescent whitening agents are Tinopal® DMS and Tinopal® CBS available from Ciba-Geigy AG, Basel, Switzerland. Tinopal® DMS is the disodium salt of 4,4'-bis-(2-morpholino-4 anilino-s-triazin-6-ylamino) stilbene disulphonate. Tinopal® CBS is the disodium salt of 2,2'-bis-(phenyl-styryl)disulphonate.

Also preferred are fluorescent whitening agents of the structure:

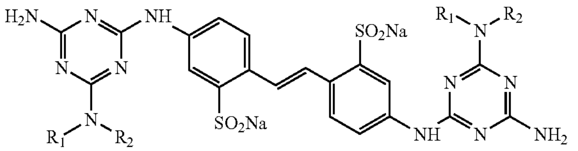

wherein R1 and R2, together with the nitrogen atom linking them, form an unsubstituted or C1-C4 alkyl-substituted morpholino, piperidine or pyrrolidine ring, preferably a morpholino ring (commercially available as Parawhite KX, supplied by Paramount Minerals and Chemicals, Mumbai, India)

Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Fabric hueing agents—Dyes or pigments which when formulated in detergent compositions can deposit onto a fabric when said fabric is contacted with a wash liquor comprising said detergent compositions thus altering the tint of said fabric through absorption of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and co-pending European application no o6116780.5 filed 7 Jul. 2006.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—In addition to the bacterial alkaline endoglucanase, the cleaning compositions can comprise one or more other enzymes which provide cleaning performance and/or fabric care benefits. Examples of suitable enzymes include, but are not limited to, hemicellulases, peroxidases, proteases, other cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In a preferred embodiment, the compositions of the present invention will further comprise a lipase, for further improved cleaning and whitening performance. A typical combination is an enzyme cocktail that may comprise, for example, a protease and lipase in conjunction with amylase. When present in a cleaning composition, the aforementioned additional enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Softening system—the compositions of the invention may comprise a softening agent such as clay and optionally also with flocculants and enzymes; optionally for softening through the wash.

Colorant—the compositions of the invention may comprise a colorant, preferably a dye or a pigment. Particularly, preferred dyes are those which are destroyed by oxidation during a laundry wash cycle. To ensure that the dye does not decompose during storage it is preferable for the dye to be stable at temperatures up to 40° C. The stability of the dye in the composition can be increased by ensuring that the water content of the composition is as low as possible. If possible, the dyes or pigments should not bind to or react with textile fibres. If the colorant does react with textile fibres, the colour imparted to the textiles should be destroyed by reaction with the oxidants present in laundry wash liquor. This is to avoid coloration of the textiles, especially over several washes. Particularly, preferred dyes include but are not limited to Basacid® Green 970 from BASF and Monastral blue from Albion

EXAMPLES

| | Composition of Soap 1/weight % | Composition of Soap 2/weight % | Composition of Soap 3/ weight % | Composition of Soap 4/ weight % |
|---|---|---|---|---|
| C8-C20 fatty acid soap | 94.2 | 81.5 | 91.05 | 81.7 |
| Glycerine Content | 4.0 | 4.0 | 5.3 | 3.8 |
| Sodium Chloride | 0.8 | 0.5 | 0.65 | 0.5 |
| Free Fatty Acid | 0.0 | 0.0 | 0.0 | 0.0 |
| Moisture Content | 1 | 14 | 3 | 14 |

| Chain Length Distribution | | | | |
|---|---|---|---|---|
| | Soap 1: - 80:20 Beef Tallow: Coconut oil fatty acid chain length distribution/ weight % | Soap 2: - 80:20 Palm oil: Coconut oil fatty acid chain length distribution/ weight % | Soap 3 - 78:22 Beef Tallow: Coconut oil fatty acid chain length distribution/ weight % | Soap 4 - 80:20 Palm oil: Coconut oil Fatty acid chain length distribution/ weight % |
| C8 | 1.4 | 1.4 | 1.5 | 1.4 |
| C10 | 1.3 | 1.2 | 1.4 | 1.2 |
| C12 | 10.1 | 10.0 | 11.1 | 10.0 |
| C14 | 6.0 | 4.4 | 6.3 | 4.4 |
| C15 | 0.0 | 0.0 | 0.0 | 0.0 |
| C16' | 2.7 | 0.0 | 2.7 | 0.0 |
| C16 | 21.0 | 37.8 | 20.7 | 37.8 |
| C17 | 0.0 | 0.0 | 0.0 | 0.0 |
| C18" | 2.6 | 8.2 | 2.6 | 8.2 |
| C18' | 35.6 | 33.2 | 34.9 | 33.2 |
| C18 | 15.8 | 3.8 | 15.5 | 3.8 |
| Minors | Up to 100 | Up to 100 | Up to 100 | Up to 100 |

Example 1

A mixed composition is produced by feeding Soap 1 and Soap 2 in a weight ratio of 3:1 into a Wenger TX-85 Twin Screw Extruder with each screw having predominantly conveying screws, but with some kneading elements and reverse elements; an 85 mm screw diameter; a length to diameter ration of 19.5; and with the extruder itself having an extrusion rate of 750 kg/hr. A stream of Monastral blue dye (supplied by Albion) is then added to the mixed composition such that the combined final composition comprises 1% by weight of the Monastral blue dye. The extruder is fitted with a die comprising 201 orifices and each orifice comprises a 5.0 mm×2.7 mm elliptical hole having a 3.1 mm×1.2 mm elliptical pin inserted into the elliptical hole so as to form an elliptical annular orifice. A rotary cutter is used to cut the soap extrudate every time 0.2 mm has been extruded from each orifice. The rotary cutter has 15 blades, with each blade being 4.45 cm wide, 3.44 cm long and 0.025 mm thick. The rotary cutter is rotated at 2000 rpm. The annular orifices of the die are arranged such that their greater diameter is aligned with the cutting direction of the blades. Once formed, the circular soap rings are optionally cooled using a rotary cooler with air at 23° C. and then optionally classified by size. The shaped articles that are formed by this process are substantially circular rings.

Example 2

The same method is used as for Example 1 except in this instance a weight ratio of 50% by weight of Soap 3 and 50% by weight of Soap 4 is used to form the mixed composition. Again circular soap rings are achieved using elliptical annular orifices.

What is claimed:

1. A method for manufacturing a shaped article comprising soap, the method comprising the steps of forming a first article by extrusion; and cutting the shaped article from a first article as the first article is extruded, said cutting in a cutting plane using a tapered blade at an angle of less than 45° to the cutting plane;

wherein as the shaped article is cut from the first article the shaped article's cross-section is deformed;

and wherein the first article's cross-section is shaped such that it compensates for the deformation during the cutting step so as to achieve a shaped article with a desired cross-section.

2. A method according to claim 1 wherein the first article's cross-section is greater, with respect to the desired cross-section of the shaped article, in the cutting direction.

3. A method according to claim 1 wherein the ratio between the length of the shaped article to its greatest cross-section in the cutting plane is from 1:1 to 1:100.

4. A shaped article according to claim 1 wherein the shaped article is substantially annular.

* * * * *